United States Patent
Mathew et al.

(10) Patent No.: US 7,524,622 B2
(45) Date of Patent: Apr. 28, 2009

(54) METHODS FOR INCREASING PRODUCTION OF IFN-GAMMA IN NATURAL KILLER CELLS EXPRESSING LLT1 RECEPTOR

(75) Inventors: Porunelloor A. Mathew, Keller, TX (US); Kent S. Boles, St. Louis, MO (US)

(73) Assignee: University of North Texas Health Science Center at Fort Worth, Fort Worth, TX (US)

( * ) Notice: Subject to any disclaimer, the term of this patent is extended or adjusted under 35 U.S.C. 154(b) by 365 days.

(21) Appl. No.: 11/106,399

(22) Filed: Apr. 14, 2005

(65) Prior Publication Data

US 2006/0002892 A1 Jan. 5, 2006

Related U.S. Application Data

(60) Division of application No. 10/335,009, filed on Dec. 31, 2002, now abandoned, which is a continuation-in-part of application No. 09/475,365, filed on Dec. 30, 1999, now abandoned.

(51) Int. Cl.
*C12Q 1/00* (2006.01)
*C07K 14/555* (2006.01)
*C07K 14/435* (2006.01)
*A61K 39/395* (2006.01)

(52) U.S. Cl. .................... 435/4; 530/351; 530/350; 424/130.1

(58) Field of Classification Search .................. None
See application file for complete search history.

(56) References Cited

U.S. PATENT DOCUMENTS 6,455,683 B1 * 9/2002 Yang et al. .................. 536/23.1

OTHER PUBLICATIONS

Chuang et al., LLT1 induces IFN-gamma production but not cytotoxicity in NK cells. FASEB Journal 16(4):A707, Mar. 20, 2002.*
Boguski MS. The "Turning Point in Genome Research." Trends Biochem Sci. Aug. 1995;20 (8):295-6.
Boguski MS, Lowe TM, Tolstoshev CM. "dbEST—Database for Expressed Sequence Tags." Nat Genet. Aug. 1993;4(4):332-3.
Brown MG, Scalzo AA, Matsumoto K, Yokoyama WM. "The Natural Killer Gene Complex: a Genetic Basis for Understanding Natural Killer Cell Function and Innate Immunity." Immunol Rev. Feb. 1997;155:53-65.
Boles KS, Barten R, Kumaresan PR, Trowsdale J, Mathew PA. "Cloning of a New Lectin-like Receptor Expressed on Human NK cells." Immunogenetics. Oct. 1999; 50(1-2):1-7.
Bork P, Koonin EV. "Predicting Functions From Protein Sequences—Where are the Bottlenecks?" Nat Genet. Apr. 1998;18(4):313-8.
Chang C, Rodriguez A, Carretero M, Lopez-Botet M, Phillips JH, Lanier LL. "Molecular Characterization of Human CD94: a Type II Membrane Glycoprotein Related to the C-type Lectin Superfamily." Eur J Immunol. Sep. 1995; 25(9):2433-7.

EMBL Database, Accession No AF133299 (Jan. 2, 2000).
EMBL Database, Accession No AAG00514 (Aug. 17, 2000).
Hamann J, Fiebig H, Strauss M. "Expression Cloning of the Early Activation Antigen CD69, a Type II Integral Membrane Protein with a C-type Lectin Domain." J Immunol. Jun. 1, 1993;150(11):4920-7.
Hamann J, Montgomery KT, Lau S, Kucherlapati R, van Lier RA. "WAICL: A New Activation-Induced Antigen Encoded by the Human NK Gene Complex." Immunogentics. 1997;45(5):295-300.
Houchins JP, Yabe T, McSherry C, Bach FH. DNA Sequence Analysis of NKG2, a Family of Related cDNA Clones Encoding Type II Integral Membrane Proteins on Human Natural Killer Cells. J Exp Med. Apr. 1, 1991;173(4):1017-20.
Ioannou PA, Amemiya CT, Garnes J, Kroisel PM, Shizuya H, Chen C, Batzer MA, de Jong PJ. "A New Bacteriophage P1-Derived Vector for the Propagation of Large Human DNA Fragments." Nat Genet. Jan. 1994; 6(1):84-9.
Lanier LL. "NK Cell Receptors." Annu Rev Immunol. 1998;16:359-93.
Lanier LL, Chang C, Phillips JH. "Human NKR-P1A. A Disulfide-Linked Homodimer of the C-type Lectin Superfamily Expressed by a Subset of NK and T Lymphocytes." J Immunol. Sep. 15, 1994;153(6):2417-28.
Lazetic S, Chang C, Houchins JP, Lanier LL, Phillips JH. "Human Natural Killer Cell Receptors Involved in MHC Class I Recognition are Disulfide-Linked Heterodimers of CD94 and NKG2 Subunits." J Immunol. Dec. 1, 1996;157(11):4741-5.
Lee SH, Clark JB. "High-Yield Method for Isolation of Lambda DNA." Biotechniques. Oct. 1997;23(4):598-600.
Long EO, Wagtmann N. "Natural Killer Cell Receptors." Curr Opin Immunol. Jun. 1997;9(3):344-50.
Lopez-Cabrera M, Santis AG, Fernandez-Ruiz E, Blacher R, Esch F, Sanchez-Mateos P, Sanchez-Madrid F. "Molecular Cloning, Expression, and Chromosomal Localization of the Human Earliest Lymphocyte Activation Antigen AIM/CD69, a New Member of the C-Type Animal Lectin Superfamily of Signal-Transmitting Receptors." J Exp Med. Aug. 1, 1993;178(2):537-47.

(Continued)

*Primary Examiner*—Ruixiang Li
(74) *Attorney, Agent, or Firm*—Jackson Walker L.L.P.

(57) ABSTRACT

Natural killer (NK) cells possess the inherent capacity to kill various tumor and virally infected cells. A large family of NK cell receptors belongs to the C-type lectin super-family. Genes in the NK gene complex encode type II receptors and examples include the families of NKR-P1, Ly-49, and NKG2 receptors. Examples of other C-type lectin-like receptors that occur as individual genes are CD94, CD69 and AICL. The invention includes a cDNA that encodes a predicted protein of 191 amino acid residues having similarity to the carbohydrate recognition domain of C-type lectins. The predicted protein of LLT1 shows 59 and 56% similarity to AICL and CD69, respectively. A monoclonal antibody (L9.7) against LLT1 receptor was generated. Binding of mAb L9.7 to surface LLT1 induced interferon gamma production in YT, a human NK cell line, as well as in resting and IL-2 activated NK cells, without modulating cytotoxicity.

4 Claims, 9 Drawing Sheets

OTHER PUBLICATIONS

Poggi A, Costa P, Morelli L, Cantoni C, Pella N, Spada F, Biassoni R, Nanni L, Revello V, Tomasello E, Mingari MC, Moretta A, Moretta L. "Expression of Human NKRP1A by CD34+ Immature Thymocytes: NKRP1A-Mediated Regulation of Proliferation and Cytolytic Activity." Eur J Immunol. Jun. 1996;26(6):1266-72.

Santis AG, Lopez-Cabrera M, Hamann J, Strauss M, Sanchez-Madrid F. "Structure of the Gene Coding for the Human Early Lymphocyte Activation Antigen CD69: a C-Type Lectin Receptor Evolutionarily Related with the Gene Families of Natural Killer Cell-Specific Receptors." Eur J Immunol. Jul. 1994;24(7):1692-7.

SPTREMBL Database, Accession No. Q9UHP7 (May 1, 2000).

Testi R, D'Ambrosio D, De Maria R, Santoni A. "The CD69 Receptor: A Multipurpose Cell-Surface Trigger for Hematopoietic Cells." Immunol Today. Oct. 1994;15(10):479-83.

Weis WI, Taylor ME, Drickamer K. "The C-Type Lectin Superfamily in the Immune System." Immunol Rev. Jun. 1998;163:19-34.

Wilson MJ, Torkar M, Trowsdale J. "Genomic Organization of a Human Killer Cell Inhibitory Receptor Gene." Tissue Antigens. Jun. 1997; 49(6):574-9.

Wong S, Freeman JD, Kelleher C, Mager D, Takei F. "Ly-49 Multigene Family. New Members of a Superfamily of Type II Membrane Proteins with Lectin-Like Domains." J Immunol. Aug. 15, 1991;147(4):1417-23.

Yabe T, McSherry C, Bach FH, Fisch P, Schall RP, Sondel PM, Houchins JP. "A Multigene Family on Human Chromosome 12 Encodes Natural Killer-Cell Lectins." Immunogenetics. 1993;37(6):455-60.

Yokoyama WM, Seaman WE. "The Ly-49 and NKR-P1 Gene Families Encoding Lectin-Like Receptors on Natural Killer Cells: The NK Gene Complex." Annu Rev Immunol. 1993;11:613-35.

Ziegler SF, Ramsdell F, Hjerrild KA, Armitage RJ, Grabstein KH, Hennen KB, Farrah T, Fanslow WC, Shevach EM, Alderson MR. "Molecular Characterization of the Early Activation Antigen CD69: a Type II Membrane Glycoprotein Related to a Family of Natural Killer Cell Activation Antigens." Eur J Immunol. Jul. 1993;23(7):1643-8.

* cited by examiner

A

```
gaattccggcaaatgcatgacagtaccaatgtggagaagacatacaccatctgaatgcctgcaaacccaggtgtctgcattcaaaaggcattctattaagctaccttaattg 120
                          M  H  D  S  N  N  V  E  K  D  I  T  P  S  E  L  P  A  N  P  G  C  L  H  S  K  E  H  S  I  K  A  I  L  L  W gcgcttatttttctaatcatgtttctgcaatcatagtgtgtgaatggttgctgcttaagcgcaataagagcgtaactccaataagagcgtaactccatcaagagccatcaagactagagttcttcaaggctcaagtctt 240
 R  L  E  L  I  M  E  L  I  L  I  V  C  G  M  V  A  A  L  S  A  L  R  A  N  C  H  Q  E  P  S  V  C  L  Q  A  A  C  P agagagctgagttggattggtttccaagaaagtgtttctatttctgagataaaggcccatctatcactgatcactggatgatcactggatgacacaagatcagaggttcagaggttctgactcacaagatgctgatcttgctcaggtgaaagctt 360
 E  S  W  I  G  F  Q  R  K  C  F  Y  F  S  D  D  T  K  N  W  T  S  S  Q  R  F  C  D  S  Q  D  A  D  L  A  Q  V  E  S  F ccaggaactgaattcctgtttgagataaaggcccatctgatcactggatcactggatgggctgagcagaacaaggccaacatgaaatggactgaatggactgaatggacaagacagttccagcacagatcgaatggacaagacagttccagca 480
 Q  E  L  N  F  L  L  R  Y  K  G  P  S  D  H  W  I  G  L  S  R  E  Q  G  Q  P  W  K  W  I  N  G  T  E  W  T  R  Q  F  P tatcctgggagcaggagagtgtgcctattgaatgacaaaggtgccagtagtgccaggacacacacagagaggaagtggattttgttccaaatcagatatacatgtctagatgttacagca 600
 I  L  G  A  G  E  C  A  Y  L  N  D  K  G  A  S  S  A  R  H  Y  T  E  R  K  W  I  C  S  K  S  D  I  H  V aagcccaactaatcttagaagcatagtgataactccattttaaaatgaacccaggtatatgaaaatatgctcaatatcactaatactgaatctgctctcccactgtcatgacataccgagaatgagtaatttataataaaagagattaa 720 gaaaatacaaatcaaaatcatgtaaaatattacctgttttcatggctaattattacctgttctcccactgtcatgacataccgagaatgagtaatttataataaaagagattaa 840 ttgaaaaaaa                                                                                                                          850
```

METHODS FOR INCREASING PRODUCTION OF IFN-GAMMA IN NATURAL KILLER CELLS EXPRESSING LLT1 RECEPTOR

CROSS REFERENCE TO RELATED APPLICATIONS

The present invention is a divisional of U.S. patent application Ser. No. 10/335,009 filed on Dec. 31, 2002 now abandoned. The Ser. No. 10/335,009 application was a continuation-in-part of U.S. patent application Ser. No. 09/475,365, filed on Dec. 30, 1999 now abandoned. Both the Ser. Nos. 10/335,009 and 09/475,365 applications are incorporated herein by reference.

The government owns rights in the present invention pursuant to grant number P01 A1 38938 from the National Institutes of Health and grants from the EEC (CT96-1105), and the MRC.

FIELD OF THE INVENTION

The present invention relates generally to the field of specific cell surface receptors, and in particular characteristic peptides of these receptors. Even more particularly, it concerns cell surface receptor peptides on cell types important in governing immune system response, such as cells known as natural killer (NK) cells. The present invention also relates to methods of treating immune function disorders. In particular embodiments, these methods apply various of the cell surface receptor peptides identified by the present inventors in therapies directed to enhance immune cell function, and consequently provide a treatment for immune system related pathologies.

BACKGROUND OF THE INVENTION

The molecular basis of target cell recognition by NK cells is poorly understood. Unlike T and B cells, NK cells do not rearrange DNA to generate diversity. Therefore, one could predict that NK cells might express several receptors to recognize various targets or utilize some other mechanism to generate diversity. In fact, over the last few years a number of receptors have been identified on NK cells (Lanier 1998). However, all the function of NK cells could not be accounted for by the known receptors.

The C-type carbohydrate recognition domain (CRD) is the common feature among Cat++ dependent animal lectins and structurally related proteins. A subset of the C-type lectin family found on natural killer (NK) cells contains domains homologous to other C-type lectin domains, but whether they mediate interactions through carbohydrate or protein binding remains unresolved (Weis et al. 1998). NK cell receptors with lectin-like domains are encoded in the NK gene complex on Chromosome (Chr) 6 in the mouse and Chr 12 in the human. (Brown et al. 1997; Yabe et al. 1993; Yokoyama and Seaman 1993).

The majority of NK cell receptors encoded by the NK gene complex belong to groups of highly related genes such as the NKR-P1, Ly-49, and NKG2 families. The Ly-49 and NKG2 families contain members that are mostly inhibitory, but have a few members that transduce activation signals (Lanier 1998; Long and Wagtmann 1997; Yokoyama and Seaman 1993). The NKR P1 receptors have been observed to act as activating receptors in rodents. Cross-linking of the human NKR-P1 homologue with antibody leads to inconsistent results (Lanier 1998). CD94 is a type II receptor express on most NK cells and was originally implicated as an inhibitory receptor (Change et al. 1995; Long and Wagtmann 1997). Subsequently, it was discovered to form a heterodimer with members of the NKG2 family (Lazetic et al. 1996).

CD69 and AICL (activation-induced C-type lectin) are two structurally similar receptors localized to the NK gene complex, but have interesting differences from the other genes located there. As opposed to the other type II receptors in the NK gene complex, which are restricted to NK cells and a subset of T cells, CD69 and AICL are expressed in most cells of hematopoetic origin (Hamann et al. 1997; Lanier 1998; Long and Wagtmann 1997; Testi et al. 1994). The function of AICL is not know, but CD69, cross-linking leads to the activation of NK cells, T cells, B cells, monocytes, granulocytes, and platelets (Testi et al. 1994). In addition, these genes appear to have single rather than multiple isoforms.

Despite advances that have been made in the area of immune cell function, a need continues to exist in the medical arts for improved techniques for antibody tumor growth and other cancer forms such as leukemia. In addition, insofar as bone-marrow grating has been used, significant immune rejection difficulties preclude the use of these. techniques for improving and/or replacing immune function in animals, and most importantly, preventing host rejection.

SUMMARY OF THE INVENTION

The present invention, in a general and overall sense, concerns a novel cell surface receptor localized on natural killer (NK) cells.

In the present invention, the molecular cloning, characterization, and expression pattern of a new lectin-like transcript predominantly expressed on human NK cells is defined. In particular, the molecular characterization of LLT1 and LLT2 is provided in the present invention. This study describes the cloning and molecular characterization of a new member of the human NK gene complex. The conserved C-typed C-RD found in NK cells receptors localized to the NK gene complex allowed identification of related sequences in the EST database. LLT1 is localized to the human NK gene complex on Chromosome 12, close to the location of CD69. The predicted peptide of LLT1 (FIG. 1A) bears similarity to CD69 and AICL (Hamann et al. 1993, 1997; Lopez-Cabrera et al. 1993; Ziegler et al. 1993). The function of CD69 has been extensively characterized. Cross-linking with anti-CD69 Ab activates the cell-specific functions of lymphocytes, granulocytes, monocytes, and platelets (Testi et al. 1994). CD69 is a useful indicator of cell activation and immune arousal, and provides useful information as to the function of LLT1.

In some embodiments, the present invention provides a polypeptide of the LLT1 cell receptor. In one aspect, this polypeptide may be described further as comprising a transmembrane domain near the N-terminus of the polypeptide, and as having an overall length of about 185 to about 205 amino acid residues. In particular embodiments, the length of the polypeptide is about 191 amino acid residues and is essentially free of intracellular ITIM motifs, having a molecular weight of between about 25 kilodaltons and about 65 kilodaltons. In some embodiments, the transmembrane domain of the polypeptide has an amino acid sequence of SEQ ID NO1. In other embodiments, the peptide may be further defined as having a sequence of SEQ ID NO:2. The polypeptide may also be defined as further comprising an intracellular domain of a sequence defined in SEQ ID NO:3 (30 amino acids).

In some aspects, the polypeptide is defined as further comprising an extracellular domain of about 130 amino acids, wherein said extracellular domain includes at least a first putative N-linked glycosylation site and a second putative N-linked glycosylation site. The glycosylation site is located within the polypeptide at a position defined as an amino acid position 95 to an amino acid position 97 and the second putative N-linked glycosylation site is located within the polypeptide at a position defined as an amino acid position 147 to an amino acid position 149.

The polypeptide of the invention may be formulated as a pharmaceutically acceptable preparation, and particularly as a pharmaceutically acceptable preparation suitable for injection. In some aspects, the polypeptide may be further defined as having a length of about 185 amino acid residues to about 205 amino acid residues. In preferred aspects, the polypeptide may be defined as having an amino acid length of about 191 amino acid residues.

In another aspect, the invention may be defined as a natural killer cell receptor polypeptide comprising the polypeptide as described above. For example, the natural killer cell receptor polypeptide is defined as comprising the sequence of FIG. 1A.

In another embodiment the polypeptide is defined as a clone Y9A2 having a transcript LLT1, comprising a sequence as defined in FIG. 3A.

The invention also provides a method for inhibiting tumor cell growth. In some embodiments, the methods comprise the steps of administering a tumor-cell inhibiting amount of a pharmaceutically acceptable preparation comprising the polypeptide of claim 1 in a tumor-inhibiting amount; and inhibiting tumor cell growth. According to at least some aspects of the method, the pharmaceutically acceptable preparation is further defined as a physiologically acceptable injectable preparation.

The invention also provides for antibodies having binding affinity for the LLT1 receptor peptide. The antibody of the present invention may be defined as either a monoclonal antibody or as a polyclonal antibody. Methods for preparing type of antibody are know to those of skill in the art as standard antibody generating techniques and as further defined in the following examples.

The invention also defines a method for reducing natural killer cell mediated rejection of a bone-marrow graft, which comprises: obtaining bone marrow from a patient to be a receptor of a bone marrow graft; and treating the bone marrow to a pharmacologically active preparation of the natural killer cell receptor polypeptide of LLT1 to provide a treated bone marrow preparation; administering a pharmacologically active preparation of the treated bone marrow preparation to the patient.

The invention also provides various cDNA molecules for the LLT 1 receptor peptides. In one such embodiment, the cDNA has a nucleic acid sequence encoding a human lectin-like transcript (LLT1) as defined in FIG. 1A.

The invention also provides reagents, compositions, and methods that are useful for analysis of NK cell activity, for analysis of LLT1 engagement and activation, and for analysis of the inhibitory/stimulatory effects of molecules involved in the immune system response to infection. These and various features and advantages of the invention will be apparent from a reading of the following detailed description and a review of the appended claims.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1 (1A, 1B) Analysis of the cDNA sequence of LLT1. FIG. 1A, the nucleotide sequence (SEQ ID NO: 5), and predicted translation of LLT1 (SEQ ID No: 2). The transmembrane domain is underlined (SEQ ID NO: 1). Glycosylation sites in the extracellular domain are boxed (shown within SEQ ID NO: 4). FIG. 1B, Hydrophilicity plot of the LLT1 putative peptide sequence determined by the Kyte-Doolittle method.

FIG. 2 Pileup of LLT1 (SEQ ID NO: 2) and other NK cell C-type lectin superfamily receptors (SEQ ID NOS: 6-10, respectively in order of appearance). Conserved residues are shaded and putative glycosylation sites in the extracellular domains are boxed.

FIG. 3A Total RNA (20) isolated from the YAC-1, HL-60, DB; Jurkat, and YT tumor cell lines was electrophoresed in a formaldehyde agarose gel, blotted, and probed. In addition, samples were included from PBMC and LAK cultures from a healthy donor. FIG. 3B Northern blot of poly (A)+ RNA from spleen, lymph node, thymus, peripheral blood leukocytes, bone marrow, and fetal liver tissues. Both membranes were stripped and hybridized with a P-actin probe. The position of 28 S and 18 S rRNA and the size of RNA molecular standards are shown at the left and right of panels A and B, respectively.

FIG. 8A shows that anti-2B4 mAb (200 ng/ml) activates lysis of K562 target cells (open circle), as compared to YT cells incubated with control mouse IgG (200 ng/ml) (closed square). Anti-LLT1 mAb L9.7 (200 ng/ml) failed to affect cytotoxicity in the presence of 2B4-stimulated YT cells (closed triangle) or unstimulated cells (x). FIG. 8B shows the activation of activated NK cells incubated with mAb L9.7 (200 ng/ml) fails to increase cytotoxicity as opposed to LLT1 activation on freshly-isolated resting NK cells as shown in FIG. 8C. FIG. 8D shows incubation of LAK cells with mAb L9.7 failed to increase cytotoxicity against labeled P815 target cells.

DETAILED DESCRIPTION OF THE INVENTION

Figure 3:
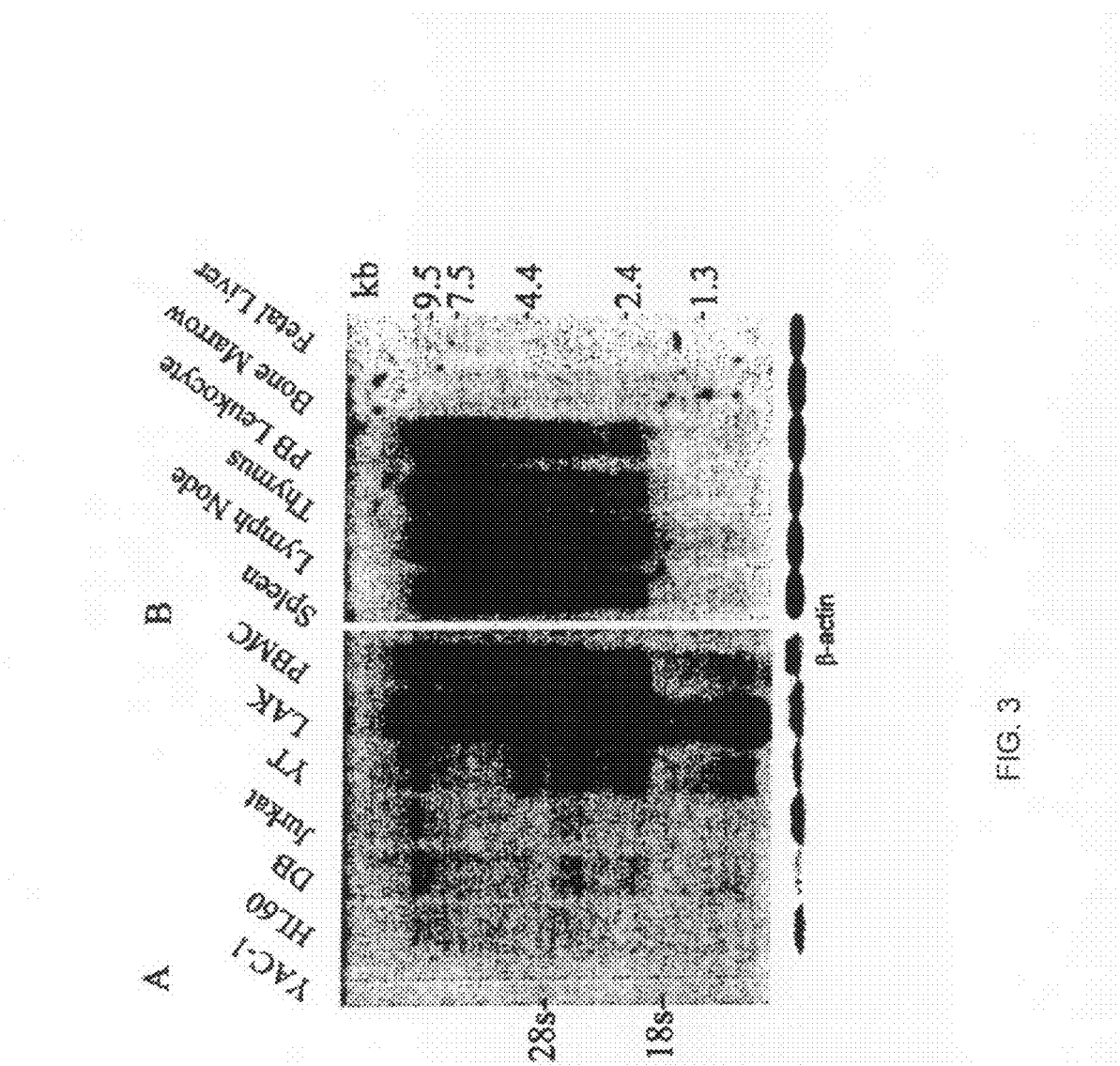
FIG. 3 (3A, 3B) RNA blot analysis of LLT1 transcripts hybridized with $^{32}$P-labeled, full length LLT1 cDNA (SEQ ID NO: 5).

Following long-standing patent law convention, the terms "a" and "an" mean "one or more" when used in this application, including the claims.

Definitions

The following definitions are provided to facilitate understanding of certain terms used herein and are not meant to limit the scope of the present disclosure.

"Antibody" refers to a Y-shaped molecule having a pair of antigen binding sites, a hinge region and a constant region. Fragments of antibodies, for example an antigen binding fragment (Fab), chimeric antibodies, antibodies having a human constant region coupled to a murine antigen binding region, and fragments thereof, as well as other well known recombinant antibodies are included in the present invention.

"Fusion protein" refers to a first protein having attached a second, heterologous protein. Preferably, the heterologous protein is fused via recombinant DNA techniques, such that the first and second proteins are expressed in frame. The heterologous protein can confer a desired characteristic to the fusion protein, for example, facilitation of purification of the fusion protein, i.e., histidine tag (6-His), GST, and the like.

"Isolated" refers to a polynucleotide or polypeptide that has been separated from at least one contaminate (polynucleotide or polypeptide) with which it is normally associated. For example, an isolated polynucleotide or polypeptide is in the context or in the form that is different from that in which it is found in nature.

Natural Killer Cells

Natural Killer (NK) cells mediate immunity against viruses, bacteria, parasites and tumors through both cellular cytotoxic mechanisms and secretion of cytokines. Trinchieri G., Adv Immunol (1989) 47:187; Cervenka et al., Nature Rev (2001) 1:41; Biron et al., Ann Rev Immunol (1999) 17:189. Large numbers of activating and inhibitory receptors are expressed on NK cells for balancing the signals that determine NK cell effector function. Lanier, L. L., Ann Rev Immunol (1998) 16:359; Moretta et al., Immunol Today (2000) 21:420. In particular, most of the inhibitory receptors recognize major histocompatibility complex (MHC) class I or MHC-like molecules expressed on target cells. Long et al., Curr Opin Immunol (1997) 9:344. In addition, recent findings indicate the involvement of activating receptors in resistance to viral infection and further that activating and inhibitory receptors can directly bind viral protein in different strains of mice. Arase et al., Science (2002) 296:1323; Brown et al., Science (2002) 292:934.

It has previously been shown that inhibitory receptors on NK cells have a common cytoplasmic feature, an immunoreceptor tyrosine-based inhibitory motif (ITIM) which have been shown to recruit the phosphatase, SHP-1. Tomasello et al., Semin Immunol (2000) 12:139. Alternatively, NK cells have demonstrated the ability to destroy tumor cells despite a significant expression of MHC class 1 molecules. Long et al., Semin Immunol (2000) 12:101; Litwin et al., J Exp Med (1993) 178:1321; Solana et al., Immunol Today (1991) 12:95. In some cases, the NK cell receptors lack ITIMs, and transmit activating signals via association with adaptor molecules that contain immunorector tyrosine-based activating motifs (ITAM). Moretta et al., Immunol Rev (1997) 155:105; Tomasello et al., Semin Immunol (2000) 12:139. Additionally, NK cell function are regulated by signals through receptors that do not recognize MHC-like ligands. Long E. O., Annu Rev Immunol (1999) 17:875; Lanier L. L., J Exp Med (2000) 191:1259; Moretta et al., Immunol Today (2000) 21:228; Moretta et al., Annu Rev Immunol (2001) 19:197. Activating receptors such as 2B4 (CD244), CD2, CD16, CS1, NKp30, NKp46 are members of the Ig superfamily and do not recognize MHC molecules. Lanier L. L., Annu Rev Immunol (1998) 16:359; Boles et al., Immunol Rev (2001) 181:234; Colonna et al., J Leukoc Biol (1999) 66:718; Mathew et al., J Immunol (1993) 151:5328; Kumaresan et al., Mol Immunol (2002) 39:1. There are also members of the lectin superfamily that transduce activating signals, such as $NKR-P_1$, Ly49 and CD69. Ryan et al., Immunol Rev (1997) 155:79; Anderson et al., Immunol Rev (2001) 181:79; Moretta et al., J Exp Med (1991) 174:1393.

Recent studies on cytokine production in NK cells reveal that there is a functional dichotomy in resting NK cells. Rajagopalan et al., J Immunol (2001) 167:1877. For example, the killer cell Ig-like receptor KIR2DL4 induced IFN-gamma production, but not cytotoxicity by resting NK cells, whereas in activated NK cells both cytokine production and cytotoxicity were induced by 2DL4 stimulation. These results show that resting NK cells behave differently than activated NK cells, upon activation through specific receptors.

As described in greater detail below, the anti-LLT1 antibodies of the present invention can be used to activate cytokine production in NK cells.

Antibodies

The LLT1 polypeptides of the present invention, in whole, in part, or as fusion proteins, were used to raise polyclonal and monoclonal antibodies that are useful in diagnostic assays for activating IFN-gamma secretion by NK cells and for the detection of LLT1 expression in PBMC. In addition, the anti-LLT1 antibodies are useful as reagent tools for characterizing the molecular actions of the LLT1 polypeptide. In preferable embodiments, a purified GST-LLT1 fusion protein is used in preparation of antibodies, using conventional techniques. Methods for the production of polyclonal and monoclonal antibodies are known in the art, see for example, Antibodies: A Laboratory Manual, Harlow and Land (eds.), (1988) Cold Spring Harbor Laboratory Press, Cold Spring Harbor, N.Y.; Monoclonal Antibodies, Hybridomas: A New Dimension in Biological Analysis, Kennet et al. (1980) Plenum Press, N.Y.

The present invention also provides a monoclonal antibody termed L9.7 as described in more detail in the Examples that follow. L9.7 was prepared by immunizing AKR/J2 mice using bacterially expressed GST-LLT1 fusion protein. The L9.7 antibody shows specific binding to LLT1 expressed on YT and LLT1 stably transfected BW cells.

Cytokine Production

Polyclonal and monoclonal antibodies of the present invention, for example the L9.7 antibody, are used to stimulate production of cytokines, for example IFN-gamma, from NK cells. NK cells are treated with 50 to 750 ng/ml anti-LLT1 antibody for a period of time, preferably from 14 to 20 hours, to maximize antibody-LLT1 interaction. Preferably, cell incubation is performed in a 5% $CO_2$ incubator. Cytokines are isolated and purified from the supernatant using conventional methods.

Assays

Agents that modify, for example, increase or decrease LLT1 mediated stimulation of NK cells can be identified, for example, by assay of L9.7 binding to LLT1 receptor and analysis of IFN-gamma production. Incubation of NK cells in the presence of L9.7 and in the presence and absence of a test agent, and correlation of IFN-gamma production with LLT1 activity or inhibition permits screening of such agents. Lower IFN-gamma production in the presence of the test agent than in the absence of the test agent indicates that the test agent has decreased the activity of LLT1. Higher IFN-gamma production in the presence of the test agent than in the absence of the test agent indicates that the test agent has increased the activity of LLT1.

Pharmaceutical Compositions

The invention provides pharmaceutical compositions containing a substantially purified anti-LLT1 antibody of the invention, for example L9.7, and a pharmaceutically acceptable carrier. Such pharmaceutical compositions are administered to cells, tissues, or patients, for example, to induce the activity of LLT1 expressing cells, including NK cells, PMNCs, etc; to induce the production of cytokines, for example IFN-gamma The invention also provides reagents, compositions, and methods that are useful for analysis of NK cell activity; for analysis of LLT1 receptor engagement and activation. and for analysis of the inhibitory/stimulatory effects of signal molecules involved in the NK cell response to infection and to tumor cells.

Therapeutic Applications

The anti-LLT1 antibodies of the invention are effective NK cell cytokine production agents. In the methods of the invention, the NK cell stimulating effects of anti-LLT1 antibodies are achieved by treating NK cells with various amounts of the anti-LLT1 antibody, and preferably with 50 to 750 ng/ml amounts of the anti-LLT1 antibody. Anti-LLT1 antibody stimulation of NK cells will produce cytokines that activate other components of the immune system, and is therefore useful in the treatment in viral infections, bacterial infections, certain auto-immune disorders, and certain types of tumor cell treatments.

The antibodies of the invention can be formulated as pharmaceutical compositions and administered to a host, preferably mammalian host, including a human patient, in a variety of forms adapted to the chosen route of administration. The compositions are preferably administered in combination with a pharmaceutically acceptable carrier, and may be combined with or conjugated to special delivery signals, including tumor targeting agents.

The antibodies of the present invention can be administered by known techniques, such as orally, parentally, by inhalation spray, topically, by absorption through a mucous membrane, or rectally, in dosage unit formulations containing conventional non-toxic pharmaceutically acceptable carriers, adjuvants or vehicles. Pharmaceutical compositions of the invention can be in sterile injectable preparations, such as sterile injectable aqueous or oleaginous suspensions and suppositories.

For an oral administration as a suspension, the compositions can be prepared according to techniques well-known in the art of pharmaceutical formulation. The compositions can contain microcrystalline cellulose for imparting bulk, alginic acid, or sodium alginate as a suspending agent, methylcellulose as a viscosity enhancer, and sweeteners or flavoring agents. As immediate release tablets, the compositions can contain microcrystalline cellulose, starch, magnesium stearate and lactose or other excipients, binders, extenders, disintergrants, diluents and lubricants known in the art.

For administration by inhalation or aerosol, the compositions can be prepared according to techniques well-known in the art of pharmaceutical formulation. The compositions can be prepared as solutions in saline, using benzyl alcohol or other suitable preservatives, absorption promoters to enhance bioactivity, fluorocarbons or other solubilizing or dispersing agents known in the art.

For administration as injectable solutions or suspensions, the compositions can be formulated according to techniques well-known in the art, using suitable dispersing or wetting and suspending agents, such as sterile oils, including synthetic mono- or diglycerides, and fatty acids, including oleic acid.

Solutions or suspensions of the compounds can be prepared in water, PBS, or other like materials. Solutions can include surfactants. Dispersions may also be prepared in glycerol, liquid polyethylene, glycols, oils, triacetin and mixtures thereof. Under ordinary conditions of storage and use, these preparations may contain a preservative to prevent the growth of microorganisms.

In addition, the dosage form of the compositions should be sterile, fluid and stable under the conditions of manufacture and storage. The proper fluidity of the compositions of the present invention can be maintained, for example, by the formulation of liposomes, or by use of non-toxic surfactants. The prevention of microorganism growth can be accomplished by inclusion of various anti-bacterial and anti-fungal agents, for example, parabens, chlorobutanol, thimerosal, and the like.

Note that within the methods of the present invention, the techniques utilized may be found in any of several well-known references, all of which are incorporated herein by reference, such as: Molecular Cloning: A Laboratory Manual (Sambrook, et al. (1980) Molecular Cloning: A Laboratory Manual); Gene Expression Technology (Methods in Enzymology, V 185, edited by D. Goeddel (1991) Academic press, San Diego, Calif.; Guide to Protein Purification in Methods in Enzymology (M. P. Deutshcer, 3d., (1990) Academic Press, Inc.); PCR Protocols: A Guide to Methods and Applications (Innis et al. (1990) Academic Press, San Diego, Calif.); and Culture of Animal Cells: A Manual of Basic Technique, Second ed. (R. I. Freshney (1987) Liss, Inc., N.Y.).

Having generally described the invention, the same will be more readily understood by reference to the following examples, which are provided by way of illustration and are not intended as limiting.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLES

Example 1

Expressed Sequence Tag Database Search and cDNA Library Screening

The expressed sequence tag (EST) database at GenBank was searched with the TblastN program vs. a consensus sequence of human (CD69, CD94, and NKG2's) and mouse (Ly-49's) C-type lectin receptors (Boguski et al. 1993, 1995). Several overlapping clones were identified and polymerase chain reaction (PCR) primers were designed to amplify a 350 base pair (bp fragment within the C-type lectin CRD. CDNA from a NK cell library constructed in X phage by J. Houchins (R & D Systems, Minneapolis, Minn., and kindly provided by A. Brooks, NIH, Bethesda, Md.) was successfully used as template. PCR cycle conditions were 94° C. for 30 s, 50° C. annealing temperature for 30 s, and a 72° C. extension for 45 s repeated for 30 cycles using Taq DNA polymerase from GIBCO BRL (Grand Island, N.Y.) at 2 MM MgC12. The same library was then screened with the resulting PCR fragment labeled with a320 d/ct0 (Feinberg and Vogelstein 1983; Sambrook et al. 1989). Approximately 5×105 clones were screened. After three rounds of screening, phage DNA was isolated from positive clones by the method of Lee and Clark (1997). All positively selected clones were sequenced (Automated sequencing facility, Department of Pathology, UT Computer Group, Wisconsin package). One clone (Y9A2) which contained an open reading frame was identified for further study. The transcript was named LLT1 (lectin-like transcript 1) due to sequence similarity to other C-type lectin-like receptors found on NK cells.

Example 2

Cell Culture

Human tumor cell lines Jurkat (T cell), YT (NK cell), HL-60 (monocytic), and DB (B cell), in addition to a murine lymphoma cell line (YAC-1), were cultured in RPMI 1640 supplemented with 10% fetal calf serum (Hyclone, Logan, Utah), 2 MM L-glutamine, 100. Units/ml of penicillin and steptomycin, 1 mM sodium pyruvate, and 0.1 mM non-essential. amino acids (Gibco BRL). A lymphokine-activated killer cell (LAK) culture was obtained by isolating peripheral blood mononuclear cells (PBMC) from 60 ml of venous blood from a healthy donor by Ficol-Paque centrifuigation (Pharmacia, Pescataway, N.J.). The cells were grown in the above media supplemented with 1000 Units/ml of human rIL-2 for three days. The non-adherent cells were removed and the culture was continued in 500 Units/ml of human rIL-2 and conditioned media until day 10, when RNA was extracted. All cell lines were grown to one million per ml and split 1:2 24 h before RNA isolation.

Example 3

RNA and DNA Blot Analysis

Total RNA was isolated with the RNAstate 60 reagent according to the manufacturer's protocol (Teltest Inc., Friendswood, Tex.), divided into 20 ug aliquots, and stored in 70% EtOH at −80° C. until used. One percent agarose gels for northern analysis were stained with ethidium bromide after electrophoresis to insure equal loading by comparison of rRNA. Northern blots were probed with 25 ng of the full-length cDNA labeled with a $^{32}$P dCTP (Feinberg and Vogelstein 1983; Sambrook et al. 1989). The first blot consisted of 20 ug of total RNA from human monocytic, T, B, and NK cell lines (HL-60, Jurkat, DB, and YT, respectively), a mouse cell line (YAC-1), and LAC and PBMC cells from a healthy donor immobilized on Hybond nylon (Amersham, Arlington Heights, Ill.). Prehybridization and hybridizations were performed according to the instructions of Amersham for the Hybond nylon membrane at 65° C. The second membrane was purchased from Clontech (Palo Alto, Calif.) and contained mRNA samples from human spleen, lymph node, thymus, peripheral blood leukocytes, bone marrow, and fetal liver (human immune system multiple tissue northern blot II). It was hybridized according to the manufacturer's instructions with the included Express-Hyb Hybridization solution at 65° C. Blots were exposed to Hyperfilm (Amersham). The membrane was subsequently stripped and reprobed for Beta actin to insure equal loading.

Genomic DNA was isolated from human liver according to standard protocol (Sambrook et al. 1989). For DNA blot analysis, human genomic DNA samples (20 gg each) were digested with various restriction enzymes (BamHI, EcoRI, HindIII, and XbaI) and separated on 0.8% agarose gel by electrophoresis. The DNA was transferred to Hybond nylon membrane under alkaline conditions (0.4 N NaOH), and fixed by UV cross linking. The membrane was prehybridized for 2 h at 65° C. in hybridization buffer (1 mM ethylenediamine-tetraacetate (EDTA), 0.5 M sodium phosphate, pH 7.2, 7% sodium dodecyl sulfate (SDS), 100 gg/ml ssDNA). The probe (50 ng of the full-length cDNA labeled with a $^{32}$P dCTP) was added to the same buffer and hybridization was continued for 18 h at 65° C. (Feinberg and Vogelstein 1983; Sambrook et al. 1989). The membrane was washed with a buffer containing 40 mM sodium phosphate, pH 7.2, 1% SDS at 65° C. for 1 h. The membrane was exposed to Hyperfihn for one day (Amersham) and developed.

A gridded human PAC library (RPCII) was hybridized for 20 h with 40 ng of LLT1 (full length c DNA labeled with a $^{32}$P) (Feinberg and Vogelstein) 1983; Ioannou, et al. 1994; Sambrook et al. 1989). The membranes were washed twice with 2× standard sodium citrate, 0.1% SDS at 65° C. for 20 min and exposed to X-ray film at −70° C. for 24 h. Positive clones were provided by the Human Genome Mapping Project resource center. DNA was extracted using a Qiagen kit (Crawley, UK) according to standard protocols. PAC DNA (200 ng) was digested to excise the insert and separated on a pulse field gel with ramped switch times from 1 to 13 s at 200 V for 16 h.

PAX Polymerase Chain Reaction and Sequencing

PCR was performed in the presence of 2.5 mM $MgCl_2$ using primers designed to the cDNA sequence (RBC151, RBC130, RBC136, and RBC141; Table 1). PAC DNA was treated for 10 s at 94° C., followed by 30 cycles at 94° C. for 10 s, 55° C. for 10 s, and 72° C. for 2 min with a 10 min final extension at 72° C. The PCR products were purified using a PCR purification kit from Qiagen and sequenced on an ABI377 automated sequencer as described previously (Wilson et al. 1997)

In order to understand the mechanism by which NK cells recognize and kill target cells, the present inventors searched the EST database with a consensus sequence of human (CD69, CD94, and NKG2s) and mouse (Ly-49s) C-type lectin receptors (Boguski et al. 1993; Boguski 1995). Several overlapping clones were identified and PCR primers were designed and used in PCR to yield a 350 by fragment within the C-type lectin CRD. The primers used for PCR amplifications are given in Table 1. A human NK cell cDNA library was screened with the PCR fragment and a positive clone (Y9A2) was selected for further analysis. The clone contained a cDNA insert of 850 by with an open reading frame predicting a polypeptide of 191 amino acid residues with a type II receptor structure (Genbank accession number AF133299). The predicted protein sequence had a single transmembrane domain of 29 amino acid residues (FIG. 1A, B) and an intracellular domain of 30 amino acid residues. Additionally, it had an extracellular lectin-like domain of 132 amino acid residues which contained two putative N-linked glycosylation sites (FIG. 1A).

Figure 2:
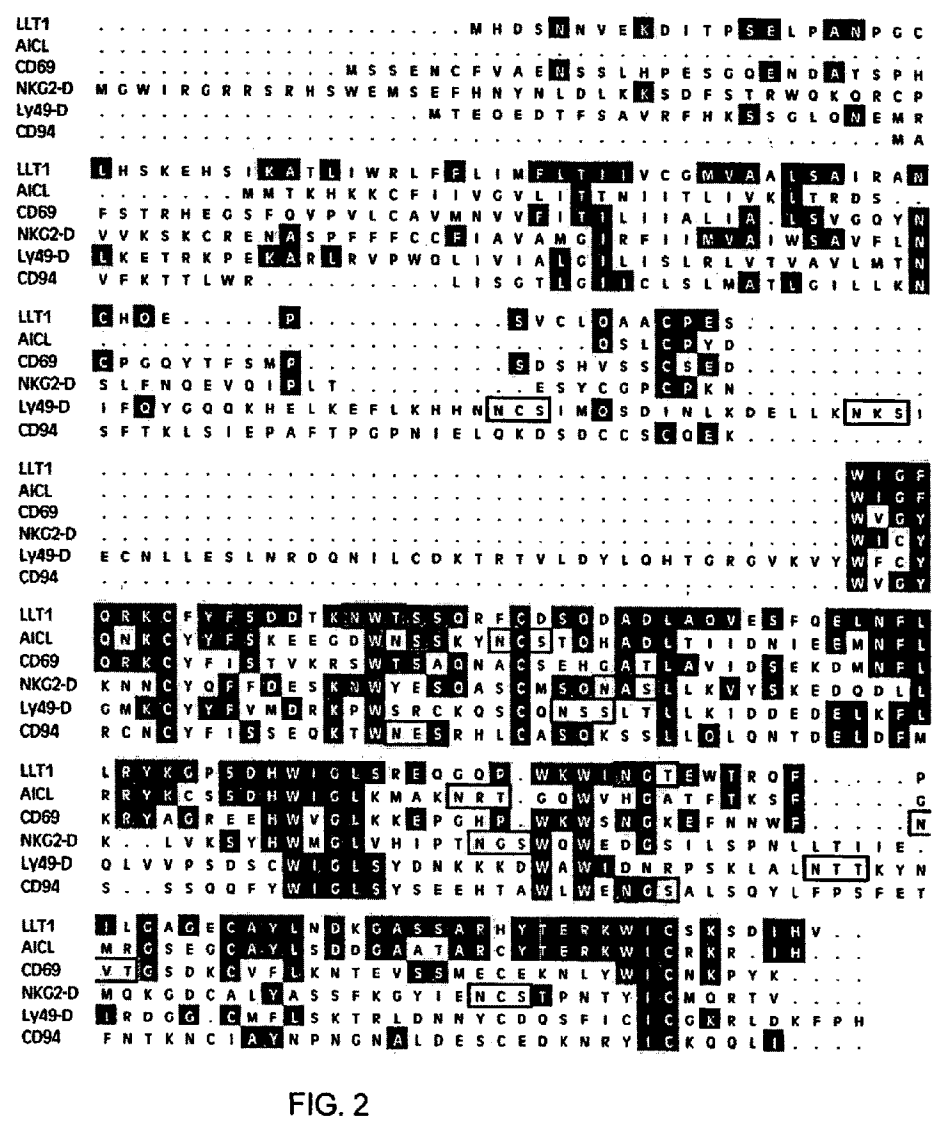

The predicted protein sequence of LLT1 has an extracellular domain with some similarity to the C-type lectin-like domains shared with other NK cell receptors (FIG. 2). It has the highest similarities to AICL and CD69 of 59 and 56%, respectively (Hamann et al. 1993, 1997; LopezCabrera et al. 1993; Ziegler et al. 1993). Representative similarities to other NK cell receptors belonging to the C-type lectin superfamily are 53, 51, and 41% to NKG2-D, CD94, and Ly-49D, respectively (Chang et al. 1995; Houchins et al. 1991; Weis et al. 1998; Wong et al. 1991).

Analysis of the sequences of LLT1 clones from another NK cell cDNA library made from pooled NK cells (NKTRP) revealed no differences, indicating that the gene is not highly polymorphic. Sequence data available in the EST database did not show variation beyond what was expected for single-pass sequences.

Example 4

Expression of LLT1 in Different Tissues and Cells

The expression of LLT1 transcripts in various cell lines and different human tissues was analyzed by northern blotting of total RNA or poly(A)+ RNA. The full-length cDNA hybridized to transcripts of approximately 5, 3.5, 2, and 0.9 kilobases (kb) in total RNA from a human NK cell line (YT) and hybridized weakly to transcripts of similar sizes from human T cell (Jurkat), B cell (DB), or monocytic (HL-60) tumor cell lines. Hybridization signals for the same size transcripts were strong in donor samples from a LAK culture and PBMC except for the 900 by transcript (FIG. 3A). Tissue distribution of LLT1 showed that human peripheral blood leukocytes, lymph node, thymus, and spleen expressed transcripts of the same relative sizes as the YT cell line with the exception of the 900 by transcript (FIG. 3B). No hybridizing transcripts were detected in mRNA from fetal liver or bone marrow. LLT1 may be expressed only in the later stages of NK cell differentiation, similar to Ly49 expression.

Figure 4:
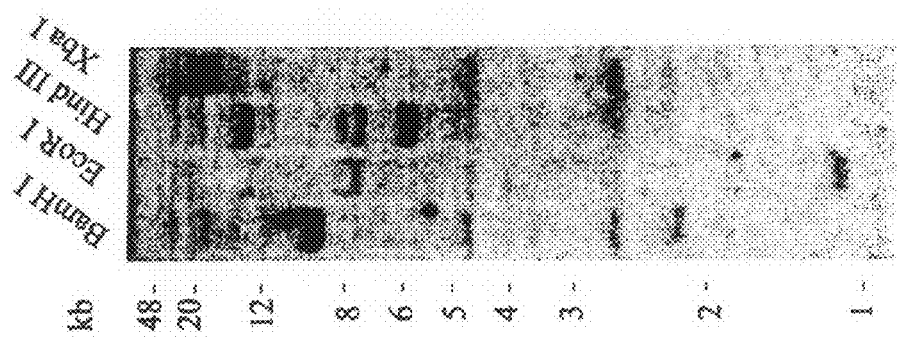
FIG. 4 Genomic DNA blot analysis of human genomic DNA from liver were digested with the restriction enzymes BamHI, EcoR1, HindIII, and XbaI, electrophoresed in 0.8% agarose, blotted, and hybridized with a $^{32}$P-labeled, full length LLT1. cDNA. Sizes of DNA standards are shown at the left.

Several lectin-like receptors expressed on NK cells belong to multigene families (Zanier 1998; Long and Wagtmann 1997; Weis et al. 1998). Southern blot analysis of human genomic DNA was carried out to explore this possibility for LLT1. Genomic DNA was isolated from human liver and digested with four different restriction enzymes (BamHI EcoRI, HindIII, and XbaI), separated on an agarose gel and transferred to a nylon membrane. The full-length LLT1 cDNA hybridized to several restriction fragments (FIG. 4). The strongly hybridizing restriction fragments identified in FIG. 4 ranged from 22 to 35 kb for the different digestions in addition to several weakly hybridizing bands.

Example 5

Chromosomal Localization

Due to the sequence similarity of LLT1 clone to AICL and CD69, LLT1 may be localized in the NK gene complex on Chr 12. Therefore, a PAC library containing the NK gene complex was screened. Two PACs were isolated from the human RCP 1 library using a probe for LLT1. The inserts of PAC NKCP4 and NKCP5 were sized on a pulsed field gel to 110 and 160 kb, respectively.

LLT1 is located in the human NK gene complex within 100 kb of the CD69 gene. PCR products of approximately 0.9 kb (RBC150/RBC130) as expected for the CD69 gene and 1.8 kb (RBC136/RBC141) for the LLT1 gene were obtained with both PAC DNAs as templates. The PCR products were sequenced. The LLT1-specific PCR product sequence revealed amplification of an intron. The exon sequence showed 100% identity to the cDNA of LLTL The presence of an intron sequence is consistent with this being the authentic LLT1 gene, and not a process pseudogene. Consistently, all CD69 sequences were observed to have three nucleotide exchanges (out of 796 bp) in comparison with the published CD69 sequence (GenBank accession number Z30428). This may be due to polymorphism in the untranslated 3' end of the gene.

The observation of multiple bands in northern analysis implies the existence of highly related transcripts or splice variants of LLT1 (FIG. 3). Both LLT1 and CD69 are expressed in lymphocytes, at a high level in NK cells and less in T and B cells (FIG. 3; Hamann et al 1993). LLT1 may be inducible on T and B cells. The restricted expression of LLT1 to tissues representing the later stages of NK cell differentiation implicates it as a receptor involved in immune response rather than development (FIG. 3B). The Southern blot showed a simple pattern indicting a single gene or a small number of genes. A somewhat similar pattern has been reported for CD69 (Santis et al. 1994) and AICL (Hamann et al. 1997). The CD69 gene is localized to approximately 20 kb. Taken together, LLT1 is likely a single gene.

The LLT1 gene was localized to within 100 kb of the CD69 gene. The AICL gene has been previously localized to 0.3 cM proximal to the CD69 gene (Hamann et al. 1997). The genes might be derived from the duplications of a common ancestral gene in view of the genes and the sequence similarities between he AICL, CD69, and LLT1 cDNAs.

Sequence analysis and chromosomal localization classify LLT1 as a new member of the NK cell receptors located in the human NK gene complex. Sequence similarity to CD69 and AICL suggest that LLT1 may have a comparable role in the immune system. Antibodies are being generated which will permit the functional role of LLT to be discerned in human lymphocytes.

Example 6

Preparation of Recombinant LLT1 Peptide Using LLT1 cDNA

The cDNA for LLT1 will be digested with restriction enzymes and cloned into a suitable protein expression vector. The expression construct plasmid will be purified and transected into E. coli by standard procedures. Expression of the recombinant peptide was performed following the expression vector supplier's recommended protocols LLT1 expression cultures would be expected to yield several milligrams of protein per liter on average. The recombinant polypeptide of 29-30 kDa will be purified by standard procedures such as polyacrylamide gel electrophoresis, isoelectric focusing, and FPLC over cation, anion, gel filtration, and/or Hydroxyapatite columns.

The purified protein will then used to generate polyclonal antibodies. New Zealand White rabbits will be immunized with 1-10 milligrams of recombinant purified LLT1 mixed with Freund's adjuvant following standard protocols. After multiple injections over several weeks, the rabbits whose sera are positive for LLT1 antibodies will be sacrificed and their sera stored at 20° C.

The purified protein will also be used to generate monoclonal antibodies. Mice (e.g. BALB/C) will be immunized with recombinant purified LLT1 mixed with Freund's adjuvant following standard protocols. After multiple injections over time, the mice will be sacrificed and fusion hybridoma cells generated using spleen derived B-cells by following standard protocols. Hybridoma cell lines will then be isolated by serial dilution cloning and lines positive for LLT1 antibodies will be identified using standard protocols.

Bacterial protein is a fusion protein used in AB products (3-gal (fan bacterial)=LLT1 as

Example 7

Production of a LLT1 Specific Monoclonal and Polyclonal Antibodies

Anti-LLT1 monoclonal and polyclonal antibodies were produced for use in further characterizing the functional properties of LLT1 (see Examples 8-11).

Expression of LLT1 fusion protein, for use in the production of LLT1 antibodies, was prepared using the LLT1 cDNA cloned into phage clone Y9A2 as a PCR template and cloning the resultant product into a pGEX-4T-1 plasmid in frame with the glutathione S-tranferase (GST) gene. The following primers were used in the PCR reaction: forward primer (containing BamHI site): 5'-AAAGGATCCAATTCCGGCAAAAT-GCAT-3' reverse primer (containing SalI site): 5'-GTCGACCTAGACATGTATATCTGATTT-3', and the product was cloned into the BamHI and SalI sites of pGEX-4T-1 in frame with the glutathione S-tranferase (GST) gene to produce GST-LLT1 fusion protein. Note that all synthesized oligonucleotides used in this Example were supplied by Integrated DNA Technologies (Coralville, Iowa). The fusion protein was purified using Glutathione Sepharose 4 Fast Flow columns (Amersham). Polyclonal and monoclonal antibodies were produced by immunizing rabbits (polyclonal) and AKR/J2 mice (monoclonal) with the purified GST-LLT1 fusion protein. Immunization protocols and antibody production and screening were performed using techniques well known in the art.

Figure 5:
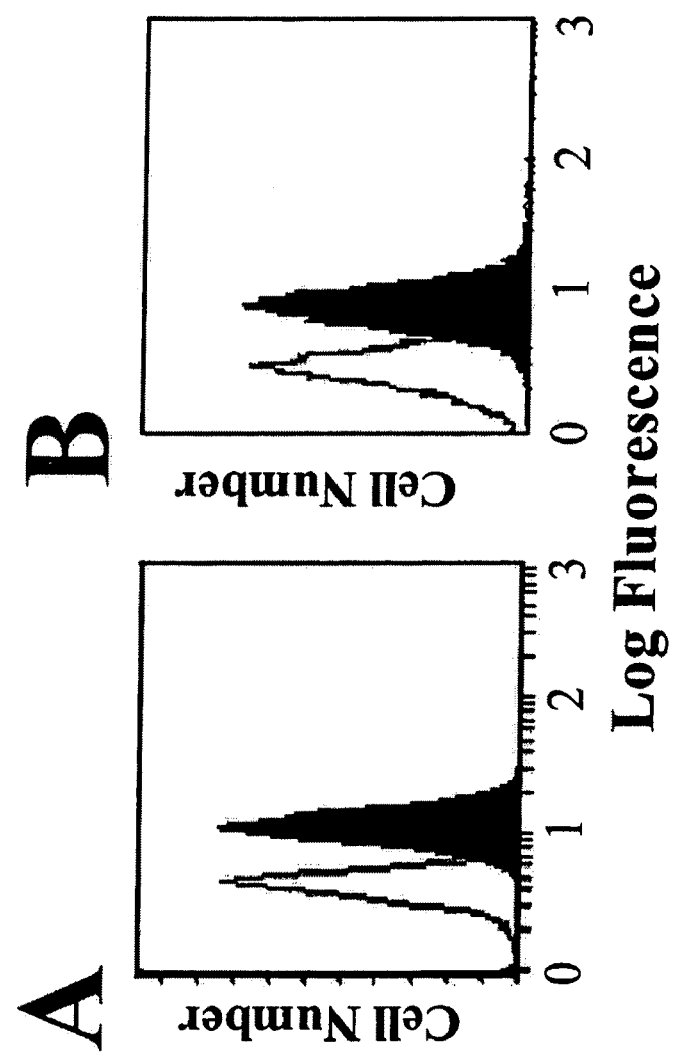
FIGS. 5A and 5B: Histogram that illustrates that mAb L9.7 recognizes LLT1 expressed on YT cells (5A) and LLT1 transfected BW cells (5B).

A positively screened mAb, L9.7, was used to further screen for binding to LLT1 expressed on YT cells (human NK tumor cell line). As shown in FIG. 5A, the YT cells were immunostained with the L9.7 (blackened histogram) followed by FITC-conjugated anti-mouse secondary Ab or FITC-conjugated anti-mouse secondary Ab only (open histogram) and analyzed by flow cytometry. The data indicates that the L9.7 mAb bound to cell surface molecules expressed on the YT cells.

To further determine specificity of the L9.7 mAb, a his-tagged fusion protein was prepared and expressed on BW cells, as follows: LLT1 cDNA was PCR amplified to contain 6Xhis tag added to the LLT1 extracellular end and inserted into a pCIneo vector (phisLLT1) for mammalian surface expression in BW cells (Invitrogen, Carlesbad, Calif.). The histidine tag was added at the C-terminal with the reverse primer 5'-AGCGGATCCTCAATGATGATGATGGT-GATGTATAT CTGATTTGGAAC-3' (SEQ ID NO. 11), and a vector specific forward primer. BW cells (mouse T cell lymphoma) were stably transfected with phisLLT1 using Fugene 6 (Boehringer Mannheim, Indianapolis, Ind.) under G418 selection (Sigma, St. Louis, Mo.). Surface expression of hisLLT1 on transfected BW cells was verified through flow cytometry using anti-his mAb (Qiagen, Valencia, Calif.) and secondary FITC-conjugated antimouse IgG mAb (not shown).

As shown in FIG. 5B, flow cytometry analysis was performed on BW cells (open histogram) and BW cells transfected with phisLLT1 (blackened histogram) and immunostained with anti-LLT I MAb L9.7. This Example shows that a hybridoma cell line produces a specific anti-LLT1 mAb, L9.7, able to recognize cell surface expressed LLT1 receptor. The data also indicates that LLT I in YT cells is expressed as a cell surface receptor.

Example 8

Monoclonal and Polyclonal Antibodies Identify LLT1 as a Dimer on NK Cells and Transfected BW Cells As an initial point, all cells were cultured in culture media composed of RPMI 1640 supplemented with 10% fetal bovine serum (FBS) (Hyclone, Logan, Utah) having 2 mM glutamine, 100 U/ml penicillin, 100 U/ml streptomycin, 10 mM HEPES, and 10 mM non-essential amino acids. Cells were maintained at 37° C. in a humidified 5% $CO_2$/95% air incubator. Cell culture reagents were obtained from Life Technologies (Gaithersburg, Md.).

Cells were lysed with lysis buffer (1% Nonidet P-40, 0.5% deoxycholate, 0.1% SDS, 10 mM HEPES (pH 7.5), 0.15 M NaCl, 10% glycerol, 1 mM PMSF, 1 mM $Na_3VO_4$, 50 mM NaF, 1 mM EDTA, 10 mg/ml aprotinin and 10 mg/ml leupeptin. Forty micrograms of protein lysate were analyzed in 8% SDS-PAGE under reducing and non-reducing conditions. Western blots were performed according to manufacturer's chemiluminesence detection system instructions (Kirkegaard & Perry Laboratories, Gaitherburg, Md.). Western blots were hybridized with pre-immune sera, post-immune sera, and L9.7 mAb.

The mAb L9.7 and anti-LLT1 polyclonal antibodies were used in western blot analysis to determine several biochemical characteristics of LLT1. As shown in FIG. 6A, western blot analysis of LLT1 in total cell lysates of YT cells is recognized by polyclonal anti-sera as a protein of approximately 75 kDa under reducing condition and a protein of approximately 150 kDa under nonreducing conditions in YT cell lysates, and failed to bind to untransfected BW cell lysates.

As shown in FIG. 6B, an immunoblot analysis of BW, YT and BW transfected with phisLLT1 cell lysates under non-reducing conditions with anti-LLT1 polyclonal sera identified a protein of approximately 150 kDa in YT cells, as well as in LLT1 transfected BW cells. Note that L9.7 showed no binding to untransfected BW cells. In addition mAb L9.7 identified a protein of approximately 75 kDa in YT cell lysates as well as in LLT1 transfected BW cell lysates under reducing conditions (data not shown).

Figure 6:
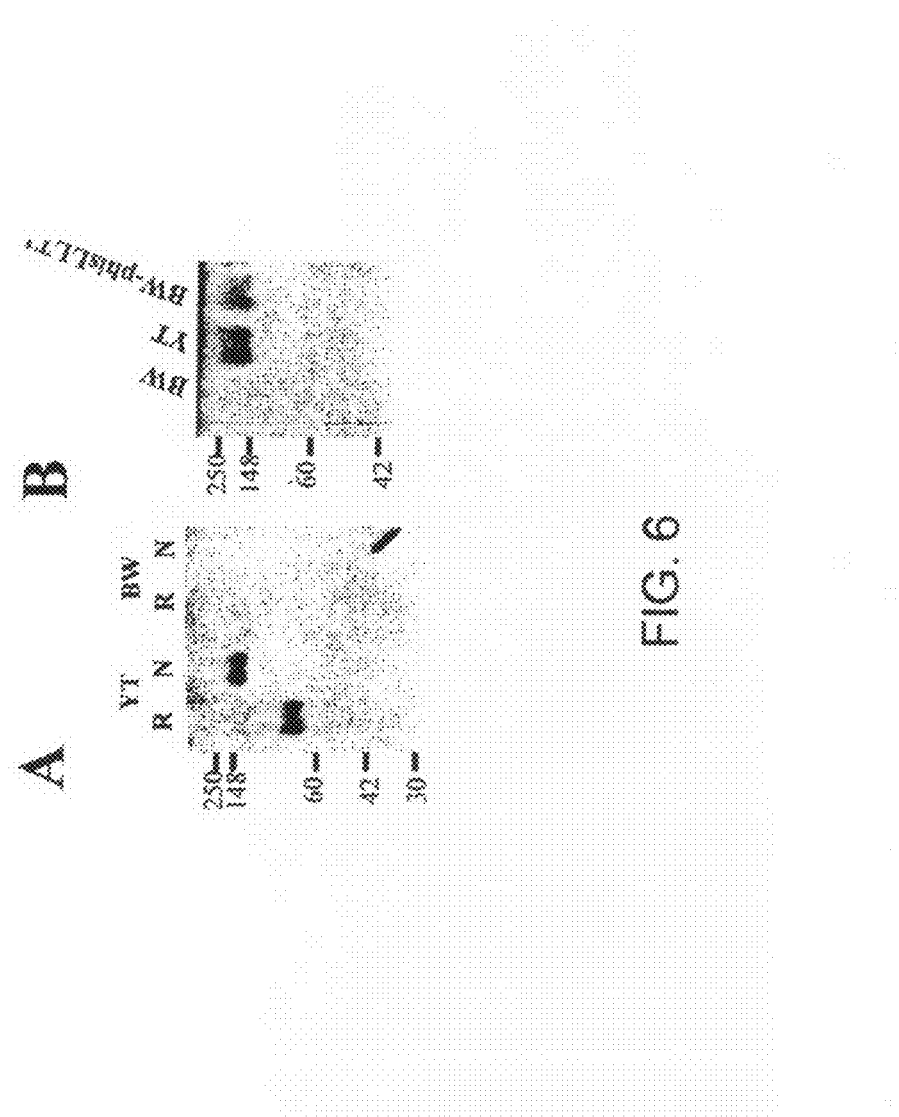
FIGS. 6A and 6B: Western blot (6A) and immunoblot (6B) analysis showing that LLT1 is expressed as a dimer on YT and LLT1 transfected BW cells.

The data in FIG. 6 indicate that a protein of approximately 75 kDa was identified by mAb in YT and BW transfectants under reducing conditions. The predicted molecular weight of LLT1 based on the amino acid sequence is 21.8 kDa. As such, the data, and presence of predicted glycosylation sites, indicate that LLT1 is heavily glycosylated, and likely expressed on the cell surface in a homodimeric form.

Example 9

LLT1 is Broadly Expressed in Peripheral Blood

The cellular distribution of LLT1 was investigated with L9.7 conjugated FITC conjugated anti-CD3, CD14, CD19, and CD56 mAbs (Becton Dickson, San Diego, Calif.).

Blood samples were isolated by venipuncture from three healthy donors. Peripheral blood mononuclear cells (PBMCs) were isolated by gradient centrifugation over Histopaque separation medium (Sigma). The L9.7 mAb was biotinylated with Sulfo-NHS-LC-biotin and subsequently detected with ImmunoPure Avidin, R—Phycoerythrin conjugated (Pierce Endogen, Rockford, Ill.). Approximately one million PBMCs were stained with L9.7 and the various CD mAbs. Additionally, monocytes were removed from the PBMCs by adherence to a plastic tissue culture flask following incubation for one hour at 37° C. One million cells per reaction of the lymphocyte-enriched fraction were subsequently labeled with L9.7 mAb in combination with either anti-CD3, -CD19, or -CD56 mAbs. Lymphocyte versus monocyte populations were differentiated by standard forward and side scatter gating. Cells were washed with PBS containing 1% BSA and analyzed on a Coulter EPICS XL flow cytometer.

Figure 7:
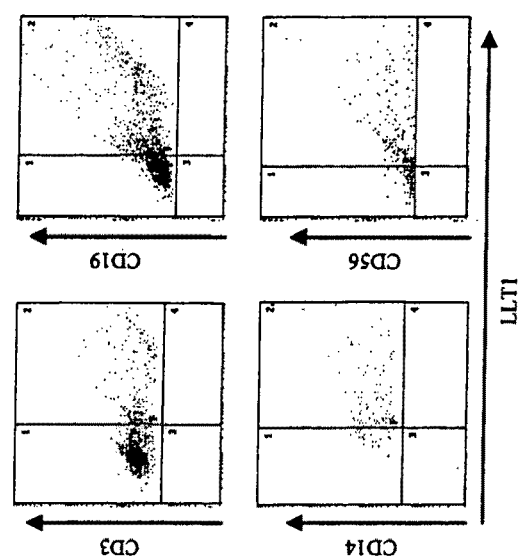
FIG. 7 Cellular distribution of LLT1 using cell sorting techniques.

As shown in FIG. 7, the cellular distribution of LLT1 was determined by labeling PBMC with L9.7 in conjugation with cell specific antibodies. In peripheral blood lymphocytes, LLT1 (PE-labeled) was detected on all three cell types. T (CD3-FITC), B (CD-19-FITC), and NK cells (CD56-FITC) expression with each cell population was 23, 50, and 71% respectively. Staining of peripheral blood mononuclear cells (CD14FITC) indicated 80% of monocytes are LLT1 positive. Lymphocyte versus monocyte populations were gated by standard forward and side scatter. Further selection was done by the markers shown and the expression of LLT1 was determined. The data indicates that LLT1 is broadly expressed in the peripheral blood.

The effect of IL-2 stimulation on LLT1 expression in NK cells was determined by stimulating isolated NK cells with 1,000 U/ml rIL-2 for four days prior to LLT1 detection (cells were alternatively treated with 10 ng/ml of PMA). Induction of LLT1 was significantly stimulated by both PMA and IL-2 stimulation (not shown), indicating that LLT1 is likely involved in cellular activation.

Example 10

LLT1 Induces Cytotoxicity by Resting NK Cells But not By Activated NK Cells or YT Cells To perform cytotoxicity assays, K562 cells (human erythroleukemia tumor cells) and P815 (mouse lymphoma tumor cells) were labeled by incubating $1 \times 10^6$ cells with 2 $Na_2{}^{51}CrO_4$ (NEN Research Products, Boston, Mass.) for 90 minutes at 37° C. under 5% $CO_2$ in air. The cells were washed three times in culture medium and subsequently were referred to as target cells. Effector YT cell suspension (100 ml) were pre-incubated in the presence and absence of 200 ng/ml anti-2B4 mAb (Coulter). Effector YT cells were resuspended and added at 1, 2, 5, 10 and 20 times the number of labeled target cells. The 2B4-stimulated and unstimulated YT cells were incubated with varying amounts of anti-LLT1 mAb for approximately one hour at 37° C. under 5% $CO_2$ prior to incubation with labeled target cells (10,000 cells in 100 ml) for four hours. After the four hour incubation, the cells were pelleted at 250× g for five minutes and 100 ml of the supernatant were removed and their radioactivity measured using scintillation.

In addition, freshly isolated NK cells and IL-2 activated NK cells were incubated with varying amounts of L9.7 and used in the $^{51}Cr$ release cytotoxicity assays as described above.

Specific lysis was calculated using the following equation: (a−b/c−b)×100, where a is the radioactivity of the supernatant of target cells mixed with effector cells, b is the radioactivity of the supernatant of target cells incubated alone, and c is the radioactivity of the supernatant after lysis of target cells with 1% Nonidet P-40 detergent.

As shown in FIG. 8A-D the engagement of LLT1 receptors increases NK cell cytotoxicity in freshly-isolated resting human NK cells but not with LAK cells or YT cells. Initially, the lysis of NK-sensitive target K562 cells by YT cells was unaffected by the presence of L9.7. To test the effect of LLT1 cross-linking with an activating receptor, effector YT cells were incubated with L9.7 and anti-2B4 mAb prior to the introduction of target cells (ligation of surface 2B4 with mAb has been previously shown to increase YT mediated destruction of target K562 cells. Boles et al., Tissue Antigens (1999) 54:27; Chuang et al, Immunology (2000) 100:378). As shown, 2B4-mediated cytolytic activity is significantly increased when compared to unstimulated YT cells. However, cross-linking of both LLT1 and 2B4 showed little or no effect on lysis when compared to ligatioin of 2B4 alone. Further, even incubating YT cells with saturating amounts of L9.7 failed to alter lytic activity (data not shown).

Figure 8:
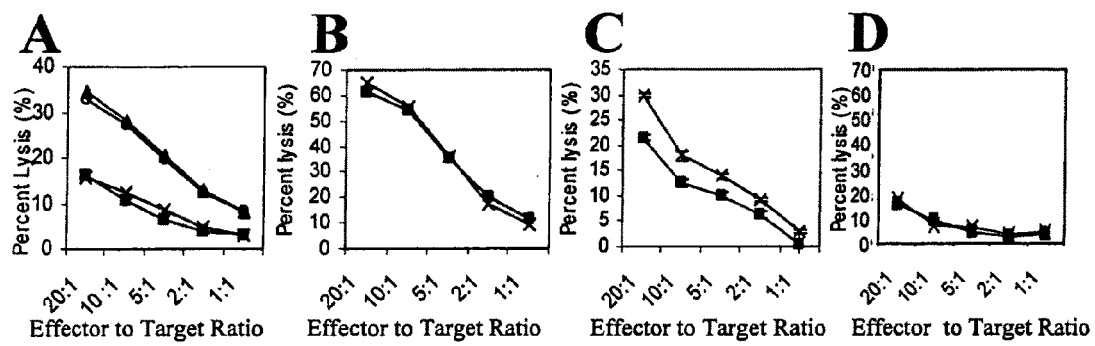
FIGS. 8A-D: Engagement of LLT1 receptors increases NK cell cytotoxicity in freshly-isolated resting human NK cells but not with activated NK cells or YT cells.

Reverse antibody dependent cellular cytotoxicity (rADCC) of FcR-positive P815 cells by YT cells in the presence of anti-2B4 mAb was significantly increased, but when increasing amounts of L9.7 mAb were added, no detectable increase in lytic activity was observed (data not shown). In addition, when IL-2 activated NK cells were used as effectors, there was little or no increase in the killing of K562 target cells in the presence of L9.7 mAb. The killing of K562 cells by activated NK cells were the same as that of the media alone at all the different effector to target (E/T) ratios tested (FIG. 8). When freshly isolated resting NK cells were used as effector cells, the presence of L9.7 increased killing of K562 target cells by about 15% at different E/T ratios. However, L9.7 did not induce redirected killing of P815 targets. LLT1 also did not show any killing of P815 cells by IL-2 activaed NK cells (FIG. 8D) as well as resting NK cells and YT cells (data not shown). The results in this Example show that LLT1 acts as an activation receptor for natural killing by resting NK cells.

Example 11

LLT1 Induces IFN-gamma Production by YT as Well as Resting and Activated NK Cells Cells (5×105) were stimulated or unstimulated with 400 ng/ml C1.7 mAb and varying amounts of anti-LLT1 mAb in flat-bottomed 24-well plates for one hour at 37° C. under 5% $CO_2$ in air. Target K562 cells (5×104) were added for 16 hours at 37° C. and 5% $CO_2$ in air, and 100 ml of cell-free supernatant collected. IFN-gamma concentration was quantitated using an ELISA, according to the manufacturer's instructions (CLB, Amsterdam, The Netherlands). Tests on each sample were performed three times.

Figure 9:
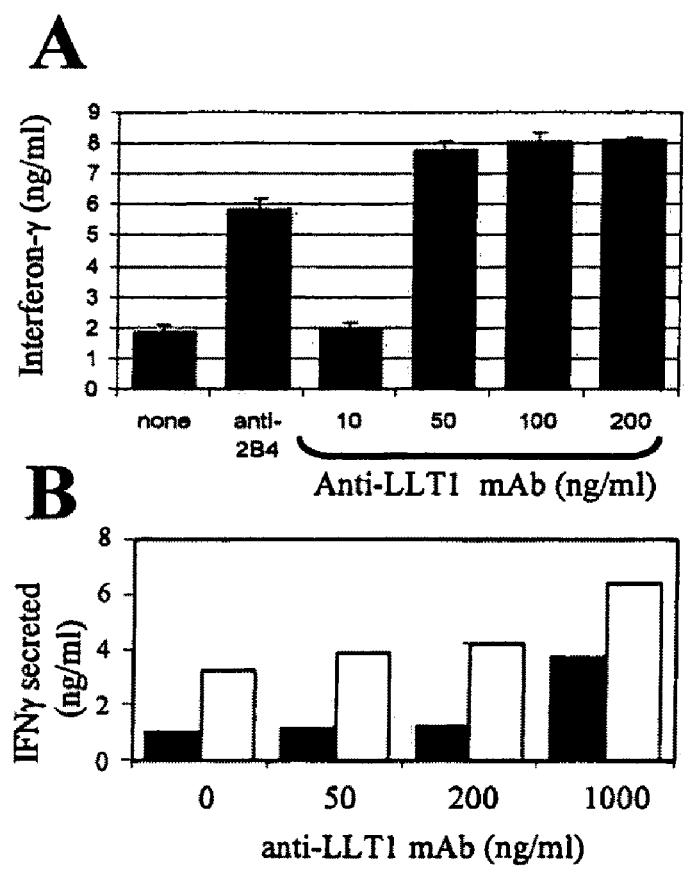
FIGS. 9A and B: Graphical showing that monoclonal antibody recognition of LLT1 results in the increased secretion of IFN-gamma in YT cells (9A) and resting NK cells (shaded bars) and activated NK cells (open bars) (9B).

It has previously been shown that NK cells are involved in immune regulation by releasing cytokines, the activity shown to be important in anti-viral, anti-proliferative, and immunomodulatory processes. Biron et al., Semin Immonol (1998) 10:383. To test the effect of LLT1/mAb ligation on IFN-gamma production by YT cells, effector YT cells and target K562 were incubated at a 10:1 ratio under varying conditions: alone, anti-2B4 mAb (200 ng/ml) or varying amounts of L9.7 (10-200 ng/ml). Cells were incubated for 16 hours and then tested for IFN-gamma production by ELISA. While the presence of anti-2B4 mAb increased the production of INF-gamma by YT cells, INF-gamma release was significantly augmented by the presence of mAb L9.7 (FIGS. 9A and B). The addition of as little as 50 ng/ml L9.7 to YT cells caused an increase in IFN-gamma secretion at levels higher than YT cell secretion of IFN-gamma when stimulated by 200 ng/ml of anti-2B4 mAb.

In addition, the effect of LLT1 ligation on freshly isolated, resting and IL-2 activated NK cells is shown. YT cells were incubated with one milliliter of culture medium alone, or culture medium with anti-2B4 mAb (200 ng/ml), or culture media with 10 to 200 ng/ml of anti-LLT1 mAb. Production of IFN-gamma was greatly induced by anti-LLT1 mAb in both resting and IL-2 activated NK cells. The induction of the IFN-gamma in resting NK cells is more dramatic than that of IL-2 activated NK cells. This is likely due to a high level of IFN-gamma production by IL-2 activated NK cells before the addition of L9.7.

The data in this Example shows that ligation of the LLT1 receptor with L9.7 induced production of IFN-gamma in resting and IL-2 activated NK cells. This is in contrast to the failure of L9.7 to induce cytotoxicity in activated NK cells (see previous Examples above). In addition, the anti-LLT1 mAb showed strong induction of IFN-gamma in YT cells, but as in the activated NK cells, showed no effect on cytolytic function.

All of the compositions and methods disclosed and claimed herein can be made and executed without undue experimentation in light of the present disclosure. While the compositions and methods of this invention have been described in terns of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein; are specifically incorporated herein by reference.

Boguski (1995), Trends Biochem Sci 20:295-296 Boguski et al. (1993), Nat Genet 4:332-333 Brown et al. (1997), Immunol Rev 155:53-65 Chang et al. (1995), Eur J Immunol 25:2433-2437 Feinberg et al. (1983), Ann Biochem 132:6-13 Hamann et al. (1993), J Immunol 150:4920-4927 Hamann et al. (1997), Immunogenetics 45:295-300 Houchins et al. (1991), J Exp Med 173:1017-1020 Ioannou et al. (1994), Nat Genet 6:84-89

Lanier (1998), Annu Rev Immunol 16:359-393 Lanier et al. (1994), J Immunol 1153:2417-2428 Lazetic et al. (1996), J Immunol 157:4741-4745 Lee et al. (1997), Biotechniques 23:598-600 Long et al. (1997), Curr Opin Immuno 19:344-350 Lopez-Cabrera et al. (1993), J Exp Med 178:537-547 Poggi et al. (1996), Eur J Immunol 26:1266-1272 Sambrook et al. (1989), Molecular cloning: A laboratory manual (2nd edn.) Santis et al. (1994), Eur J Immunol 24:1692-1697

Testi et al. (1998), Immunol Today 199415:479-483 Weis et al. (1998), Immunol Rev 163:19-34 Wilson et al. (1997), Tissue Antigens 49:574-549 Wong et al. (1991), J Immunol 147:1417-1423 Yabe et al. (1993), Immunogenetics 37:455-460

Yokoyama et al. (1993), Annu Rev Immunol 11:613-635 Ziegler et al. (1993), Eur J Immunol 23:1643-1648

What is claimed is:

1. A method for increasing the production of IFN-γ in a natural killer ("NK") cell having a LLT1 receptor comprising:
contacting the NK cell with a purified antibody that specifically binds to SEQ ID NO: 2,
wherein the purified antibody is a monoclonal antibody, and wherein the monoclonal antibody is L9.7.

2. A method for increasing the production of IFN-γ in a natural killer ("NK") cell having a LLT1 receptor comprising:
contacting the NK cell with a purified antibody that specifically binds to SEQ ID NO: 2,
wherein the NK cell is activated, and does not have increased cytotoxicity toward target cells after being contacted with the purified antibody that specifically binds to SEQ ID NO: 2, and
wherein the NK cell is activated by contacting the NK cell with a purified antibody that specifically binds to a 2B4 receptor.

3. A method for increasing the production of IFN-γ in an activated natural killer ("NK") cell having a LLT1 receptor comprising:
contacting the activated NK cell with a purified antibody that specifically binds to SEQ ID NO: 2,
wherein the activated NK cell does not have increased cytotoxicity toward target cells after being contacted with the purified antibody
wherein the purified antibody is a monoclonal antibody, and
wherein the monoclonal antibody is L9.7.

4. A method for increasing the production of IFN-γ in an activated YT natural killer ("NK") cell having an LLT1 receptor comprising:
contacting the activated NK cell with a purified monoclonal antibody L9.7 that specifically binds to SEQ ID NO.:2,
wherein the activated NK cell does not have increased cytotoxicity to target cells after being contacted with the purified monoclonal antibody L9.7, and wherein the NK cell is activated by contacting the NK cell with a purified antibody that specifically binds to a 2B4 receptor.

* * * * *

SEQUENCE LISTING

```
<160> NUMBER OF SEQ ID NOS: 10

<210> SEQ ID NO 1
<211> LENGTH: 29
<212> TYPE: PRT
<213> ORGANISM: Homo sapiens

<400> SEQUENCE: 1

Lys Ala Thr Leu Ile Trp Arg Leu Phe Phe Leu Ile Met Phe Leu Thr
 1               5                  10                  15

Ile Ile Val Cys Gly Met Val Ala Ala Leu Ser Ala Ile
            20                  25

<210> SEQ ID NO 2
<211> LENGTH: 191
<212> TYPE: PRT
<213> ORGANISM: Homo sapiens

<400> SEQUENCE: 2

Met His Asp Ser Asn Asn Val Glu Lys Asp Ile Thr Pro Ser Glu Leu
 1               5                  10                  15

Pro Ala Asn Pro Gly Cys Leu His Ser Lys Glu His Ser Ile Lys Ala
            20                  25                  30

Thr Leu Ile Trp Arg Leu Phe Phe Leu Ile Met Phe Leu Thr Ile Ile
        35                  40                  45

Val Cys Gly Met Val Ala Ala Leu Ser Ala Ile Arg Ala Asn Cys His
    50                  55                  60
```

Gln Glu Pro Ser Val Cys Leu Gln Ala Ala Cys Pro Glu Ser Trp Ile
65                  70                  75                  80

Gly Phe Gln Arg Lys Cys Phe Tyr Phe Ser Asp Asp Thr Lys Asn Trp
                85                  90                  95

Thr Ser Ser Gln Arg Phe Cys Asp Ser Gln Asp Ala Asp Leu Ala Gln
            100                 105                 110

Val Glu Ser Phe Gln Glu Leu Asn Phe Leu Arg Tyr Lys Gly Pro
        115                 120                 125

Ser Asp His Trp Ile Gly Leu Ser Arg Glu Gln Gly Gln Pro Trp Lys
    130                 135                 140

Trp Ile Asn Gly Thr Glu Trp Thr Arg Gln Phe Pro Ile Leu Gly Ala
145                 150                 155                 160

Gly Glu Cys Ala Tyr Leu Asn Asp Lys Gly Ala Ser Ser Ala Arg His
                165                 170                 175

Tyr Thr Glu Arg Lys Trp Ile Cys Ser Lys Ser Asp Ile His Val
            180                 185                 190

<210> SEQ ID NO 3
<211> LENGTH: 30
<212> TYPE: PRT
<213> ORGANISM: Homo sapiens

<400> SEQUENCE: 3

Met His Asp Ser Asn Asn Val Glu Lys Asp Ile Thr Pro Ser Glu Leu
1               5                   10                  15

Pro Ala Asn Pro Gly Cys Leu His Ser Lys Glu His Ser Ile
            20                  25                  30

<210> SEQ ID NO 4
<211> LENGTH: 132
<212> TYPE: PRT
<213> ORGANISM: Homo sapiens

<400> SEQUENCE: 4

Arg Ala Asn Cys His Gln Glu Pro Ser Val Cys Leu Gln Ala Ala Cys
1               5                   10                  15

Pro Glu Ser Trp Ile Gly Phe Gln Arg Lys Cys Phe Tyr Phe Ser Asp
            20                  25                  30

Asp Thr Lys Asn Trp Thr Ser Ser Gln Arg Phe Cys Asp Ser Gln Asp
        35                  40                  45

Ala Asp Leu Ala Gln Val Glu Ser Phe Gln Glu Leu Asn Phe Leu Leu
    50                  55                  60

Arg Tyr Lys Gly Pro Ser Asp His Trp Ile Gly Leu Ser Arg Glu Gln
65                  70                  75                  80

Gly Gln Pro Trp Lys Trp Ile Asn Gly Thr Glu Trp Thr Arg Gln Phe
                85                  90                  95

Pro Ile Leu Gly Ala Gly Glu Cys Ala Tyr Leu Asn Asp Lys Gly Ala
            100                 105                 110

Ser Ser Ala Arg His Tyr Thr Glu Arg Lys Trp Ile Cys Ser Lys Ser
        115                 120                 125

Asp Ile His Val
    130

<210> SEQ ID NO 5
<211> LENGTH: 850
<212> TYPE: DNA
<213> ORGANISM: Homo sapiens

<400> SEQUENCE: 5

```
gaattccggc aaaatgcatg acagtaacaa tgtggagaaa gacattacac catctgaatt      60
gcctgcaaac ccaggttgtc tgcattcaaa agagcattct attaaagcta ccttaatttg     120
gcgcttattt ttcttaatca tgtttctgac aatcatagtg tgtggaatgg ttgctgcttt     180
aagcgcaata agagctaact gccatcaaga gccatcagta tgtcttcaag ctgcatgccc     240
agaaagctgg attggttttc aaagaaagtg tttctatttt tctgatgaca ccaagaactg     300
gacatcaagt cagaggtttt gtgactcaca agatgctgat cttgctcagg ttgaaagctt     360
ccaggaactg aatttcctgt tgagatataa aggcccatct gatcactgga ttgggctgag     420
cagagaacaa ggccaaccat ggaaatggat aaatggtact gaatggacaa gacagtttcc     480
tatcctggga gcaggagagt gtgcctattt gaatgacaaa ggtgccagta gtgccaggca     540
ctacacagag aggaagtgga tttgttccaa atcagatata catgtctaga tgttacagca     600
aagccccaac taatctttag aagcatattg gaactgataa ctccatttta aaatgagcaa     660
agaatttatt tcttatacca acaggtatat gaaaatatgc tcaatatcac taataactgg     720
gaaaatacaa atcaaaatca tagtaaaata ttacctgttt tcatggtgct aatattacct     780
gttctcccac tgctaatgac atacccgaga atgagtaatt tataaataaa agagatttaa     840
ttgaaaaaaa                                                            850
```

<210> SEQ ID NO 6
<211> LENGTH: 149
<212> TYPE: PRT
<213> ORGANISM: Homo sapiens

<400> SEQUENCE: 6

```
Met Met Thr Lys His Lys Lys Cys Phe Ile Ile Val Gly Val Leu Ile
  1               5                  10                  15

Thr Thr Asn Ile Ile Thr Leu Ile Val Lys Leu Thr Arg Asp Ser Gln
             20                  25                  30

Ser Leu Cys Pro Tyr Asp Trp Ile Gly Phe Gln Asn Lys Cys Tyr Tyr
         35                  40                  45

Phe Ser Lys Glu Glu Gly Asp Trp Asn Ser Ser Lys Tyr Asn Cys Ser
     50                  55                  60

Thr Gln His Ala Asp Leu Thr Ile Ile Asp Asn Ile Glu Glu Met Asn
 65                  70                  75                  80

Phe Leu Arg Arg Tyr Lys Cys Ser Ser Asp His Trp Ile Gly Leu Lys
                 85                  90                  95

Met Ala Lys Asn Arg Thr Gly Gln Trp Val His Gly Ala Thr Phe Thr
            100                 105                 110

Lys Ser Phe Gly Met Arg Gly Ser Glu Gly Cys Ala Tyr Leu Ser Asp
        115                 120                 125

Asp Gly Ala Ala Thr Ala Arg Cys Tyr Thr Glu Arg Lys Trp Ile Cys
    130                 135                 140

Arg Lys Arg Ile His
145
```

<210> SEQ ID NO 7
<211> LENGTH: 199
<212> TYPE: PRT
<213> ORGANISM: Homo sapiens

<400> SEQUENCE: 7

-continued

```
Met Ser Ser Glu Asn Cys Phe Val Ala Glu Asn Ser Ser Leu His Pro
  1               5                  10                  15

Glu Ser Gly Gln Glu Asn Asp Ala Thr Ser Pro His Phe Ser Thr Arg
             20                  25                  30

His Glu Gly Ser Phe Gln Val Pro Val Leu Cys Ala Val Met Asn Val
         35                  40                  45

Val Phe Ile Thr Ile Leu Ile Ile Ala Leu Ile Ala Leu Ser Val Gly
     50                  55                  60

Gln Tyr Asn Cys Pro Gly Gln Tyr Thr Phe Ser Met Pro Ser Asp Ser
 65                  70                  75                  80

His Val Ser Ser Cys Ser Glu Asp Trp Val Gly Tyr Gln Arg Lys Cys
                 85                  90                  95

Tyr Phe Ile Ser Thr Val Lys Arg Ser Trp Thr Ser Ala Gln Asn Ala
                100                 105                 110

Cys Ser Glu His Gly Ala Thr Leu Ala Val Ile Asp Ser Glu Lys Asp
            115                 120                 125

Met Asn Phe Leu Lys Arg Tyr Ala Gly Arg Glu Glu His Trp Val Gly
        130                 135                 140

Leu Lys Lys Glu Pro Gly His Pro Trp Lys Trp Ser Asn Gly Lys Glu
145                 150                 155                 160

Phe Asn Asn Trp Phe Asn Val Thr Gly Ser Asp Lys Cys Val Phe Leu
                165                 170                 175

Lys Asn Thr Glu Val Ser Ser Met Glu Cys Glu Lys Asn Leu Tyr Trp
                180                 185                 190

Ile Cys Asn Lys Pro Tyr Lys
                195

<210> SEQ ID NO 8
<211> LENGTH: 216
<212> TYPE: PRT
<213> ORGANISM: Homo sapiens

<400> SEQUENCE: 8

Met Gly Trp Ile Arg Gly Arg Ser Arg His Ser Trp Glu Met Ser
  1               5                  10                  15

Glu Phe His Asn Tyr Asn Leu Asp Leu Lys Lys Ser Asp Phe Ser Thr
             20                  25                  30

Arg Trp Gln Lys Gln Arg Cys Pro Val Val Lys Ser Lys Cys Arg Glu
         35                  40                  45

Asn Ala Ser Pro Phe Phe Cys Cys Phe Ile Ala Val Ala Met Gly
     50                  55                  60

Ile Arg Phe Ile Ile Met Val Ala Ile Trp Ser Ala Val Phe Leu Asn
 65                  70                  75                  80

Ser Leu Phe Asn Gln Glu Val Trp Ile Pro Leu Thr Glu Ser Tyr Cys
                 85                  90                  95

Gly Pro Cys Pro Lys Asn Trp Ile Cys Tyr Lys Asn Asn Cys Tyr Gln
                100                 105                 110

Phe Phe Asp Glu Ser Lys Asn Trp Tyr Glu Ser Gln Ala Ser Cys Met
            115                 120                 125

Ser Gln Asn Ala Ser Leu Leu Lys Val Tyr Ser Lys Glu Asp Gln Asp
        130                 135                 140

Leu Leu Lys Leu Val Lys Ser Tyr His Trp Met Gly Leu Val His Ile
145                 150                 155                 160

Pro Thr Asn Gly Ser Trp Gln Trp Glu Asp Gly Ser Ile Leu Ser Pro
                165                 170                 175
```

```
Asn Leu Leu Thr Ile Ile Glu Met Gln Lys Gly Asp Cys Ala Leu Tyr
            180                 185                 190

Ala Ser Ser Phe Lys Gly Tyr Ile Glu Asn Cys Ser Thr Pro Asn Thr
            195                 200                 205

Tyr Ile Cys Met Gln Arg Thr Val
        210                 215

<210> SEQ ID NO 9
<211> LENGTH: 260
<212> TYPE: PRT
<213> ORGANISM: Homo sapiens

<400> SEQUENCE: 9

Met Thr Glu Gln Glu Asp Thr Phe Ser Ala Val Arg Phe His Lys Ser
  1               5                  10                  15

Ser Gly Leu Gln Asn Glu Met Arg Leu Lys Glu Thr Arg Lys Pro Glu
             20                  25                  30

Lys Ala Arg Leu Arg Val Pro Trp Gln Leu Ile Val Ile Ala Leu Gly
         35                  40                  45

Ile Leu Ile Ser Leu Arg Leu Val Thr Val Ala Val Leu Met Thr Asn
     50                  55                  60

Glu Cys Asn Leu Leu Glu Ser Leu Asn Arg Asp Gln Asn Ile Leu Cys
 65                  70                  75                  80

Asp Lys Thr Arg Thr Val Leu Asp Tyr Leu Gln His Thr Gly Arg Gly
                 85                  90                  95

Val Lys Val Tyr Trp Phe Cys Tyr Ile Phe Gln Tyr Gly Gln Gln Lys
            100                 105                 110

His Glu Leu Lys Glu Phe Leu Lys His His Asn Asn Cys Ser Ile Met
            115                 120                 125

Gln Ser Asp Ile Asn Leu Lys Asp Glu Leu Leu Lys Asn Lys Ser Ile
        130                 135                 140

Gly Met Lys Cys Tyr Tyr Phe Val Met Asp Arg Lys Pro Trp Ser Arg
145                 150                 155                 160

Cys Lys Gln Ser Cys Gln Asn Ser Ser Leu Thr Leu Leu Lys Ile Asp
                165                 170                 175

Asp Glu Asp Glu Leu Lys Phe Leu Gln Leu Val Val Pro Ser Asp Ser
            180                 185                 190

Cys Trp Ile Gly Leu Ser Tyr Asp Asn Lys Lys Lys Asp Trp Ala Trp
            195                 200                 205

Ile Asp Asn Arg Pro Ser Lys Leu Ala Leu Asn Thr Thr Lys Tyr Asn
        210                 215                 220

Ile Arg Asp Gly Gly Cys Met Phe Leu Ser Lys Thr Arg Leu Asp Asn
225                 230                 235                 240

Asn Tyr Cys Asp Gln Ser Phe Ile Cys Ile Cys Gly Lys Arg Leu Asp
                245                 250                 255

Lys Phe Pro His
            260

<210> SEQ ID NO 10
<211> LENGTH: 179
<212> TYPE: PRT
<213> ORGANISM: Homo sapiens

<400> SEQUENCE: 10

Met Ala Val Phe Lys Thr Thr Leu Trp Arg Leu Ile Ser Gly Thr Leu
  1               5                  10                  15
```

-continued

```
Gly Ile Ile Cys Leu Ser Leu Met Ala Thr Leu Gly Ile Leu Leu Lys
            20                  25                  30

Asn Ser Phe Thr Lys Leu Ser Ile Glu Pro Ala Phe Thr Pro Gly Pro
        35                  40                  45

Asn Ile Glu Leu Gln Lys Asp Ser Asp Cys Cys Ser Cys Gln Glu Lys
    50                  55                  60

Trp Val Gly Tyr Arg Cys Asn Cys Tyr Phe Ile Ser Ser Glu Gln Lys
65                  70                  75                   80

Thr Trp Asn Glu Ser Arg His Leu Cys Ala Ser Gln Lys Ser Ser Leu
                85                  90                  95

Leu Gln Leu Gln Asn Thr Asp Glu Leu Asp Phe Met Ser Ser Ser Gln
            100                 105                 110

Gln Phe Tyr Trp Ile Gly Leu Ser Tyr Ser Glu Glu His Thr Ala Trp
        115                 120                 125

Leu Trp Glu Asn Gly Ser Ala Leu Ser Gln Tyr Leu Phe Pro Ser Phe
    130                 135                 140

Glu Thr Phe Asn Thr Lys Asn Cys Ile Ala Tyr Asn Pro Asn Gly Asn
145                 150                 155                 160

Ala Leu Asp Glu Ser Cys Glu Asp Lys Asn Arg Tyr Ile Cys Lys Gln
                165                 170                 175

Gln Leu Ile
```